(12) United States Patent
Geesin et al.

(10) Patent No.: US 6,750,028 B1
(45) Date of Patent: *Jun. 15, 2004

(54) ANTI-FIBROTIC AGENT ASSAY

(75) Inventors: Jeffrey C. Geesin, Doylestown, PA (US); Anna Gosiewska, Belle Mead, NJ (US)

(73) Assignee: Ethicon, Inc, Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 982 days.

(21) Appl. No.: 08/957,038

(22) Filed: Oct. 24, 1997

Related U.S. Application Data (60) Provisional application No. 60/029,632, filed on Oct. 25, 1996.

(51) Int. Cl.[7] .................. G01N 33/68; C07K 14/495; A61K 31/739; C12N 5/06
(52) U.S. Cl. ............... 435/7.24; 435/70.3; 435/355; 435/366; 424/282.1; 424/531; 536/55.1; 530/350
(58) Field of Search ............... 435/7.21, 7.24, 435/70.3, 366, 355; 530/350; 424/198.1, 282.1, 531; 536/55.1

(56) References Cited

U.S. PATENT DOCUMENTS

| 5,407,913 A | 4/1995 | Sommer et al. ............ 514/121 |
| 5,525,593 A | 6/1996 | Lake et al. ................ 514/21 |
| 5,844,085 A | * 12/1998 | Purchio et al. ............ 530/351 |

FOREIGN PATENT DOCUMENTS

| EP | 466315 A | 7/1992 |

OTHER PUBLICATIONS

Meager A. Assays for transforming growth factor . J Immunol Methods Jul. 26, 1991;141(1):1–14.*

Dhanani et al. Interferon–alpha inhibits murine macrophage transforming growthfactor–beta mRNA expression. Inflammation, (Jun. 1994) 18 (3) 301–9.*

ATCC Cell Lines & Hybridomas. Paperback, 632 Pages, Edition No. 08, American Type Culture Collection, ISBN: 0930009541, Editor: Hay, Robert / Chen, T. R. / Macy, Marvin / McClintock, Patrick / Reid, Yvonne / Caputo, Jane. 1994, p. 337.*

Adams, D.O. "Macrophages", Chapter 43, In, Cell Culture (Methods of Enzymology, vol. 58, pp. 494–506), by William B. Jakoby and Ira H. Pastan (Editors), (Mar. 1979), Academic Press.*

Twardzik et al. Gamma–interferon–induced activation of latent transforming growth factor–beta by human monocytes. Annals of the New York Academy of Sciences, (1990) 593 276–84.*

Nunes et al. Characterization of latent TGF–beta activation by murine peritoneal macrophages. J. Immunol., (Aug. 1, 1995) 155 (3) 1450–9.*

Beauchamp et al. Phenotypic alterations in fibroblasts and fibrosarcoma cells that overexpress latent transforming growth factor–beta 1. Endocrinology, (May 1992) 130 (5) 2476–86.*

Supplemental Partial European Search Report, Application No. EP 97 94 9342. Place of Search—The Hague, Date of completion of the search: Aug. 10, 2001.

B. Cullen et al. "The Differential Regulation and Secretion of Proteinases from Fetal and Neonatal Fibroblasts by Growth Factor",Int. J. Biochem. Cell Biol. (1997) vol. 29, pp. 241–250.

S. Kojima et al. "Requirement for Transglutaminase in the Activation of Latent Transforming Growth Factor–$\beta$ in Bovine Endothelial Cells", The Journal of Cell Biology, vol. 121, No. 2, 1993, 439–448.

R. Flaumenhaft et al. (1993) "Activation of Latent Transforming Growth Factor $\beta$", Advances in Pharmacology, vol. 24, pp. 51–76.

Miyazono, K., et al., "A role of the latent TGF–$\beta$–binding protein in the assembly and secretion of TGF–$\beta$" EMBO J., 10:1091–1101.

Brown, P.D., et al. "Physiochemical activation of recombinant latent transforming growth factor–betas 1,2 and 3" Growth Factors, 1990, 3:35–43.

Miyazono, K., et al. "Role for carbohydrate structures in TGF–$\beta$1 latency", Nature 1989, 338: 158–160.

Miyazano K., et al. "Latent high molecular weight complex of transforming growth factor $\beta$1,purification from human platelets and structural characterization", J. Biol. Chem., 1988, 263:6407–6415.

Pircher R. et al., "$\beta$–transforming growth factor is stored in human blood platelets as a latent high molecular weight complex", Biochem. Biopsy. Res. Comm. 1989, 163:56–63.

(List continued on next page.)

*Primary Examiner*—David S. Romeo (57) ABSTRACT

A novel method has been developed for screening anti-scarring and anti-fibrotic agents. This method offers simplicity, it is reproducible and could be adopted to screen large numbers of new potential ant-fibrotic agents. This method has characteristics in common with the BAEC/BASMC co-culture system, but is more sensitive and does not require screening large number of clonal lines for developing an effective method. In this system, similar to the co-culture system, activation of L-TGF-$\beta$1 occurs by several independent mechanisms which involve binding of the latent complex to M6P/IGF-II receptors, thrombospondin and/or tissue type II transglutaminase. But, in contrast to the co-culture system, this macrophage-dependent system does not appear to involve plasmin. Using this method, potential novel anti-fibrotic agents such as IGF-II, (used separately or in combination with IGFBP-2 as a delivery vehicle) tissue type II transglutaminase inhibitors and anti-inflammatory agents (such as hydrocortisone) were identified. A potential novel mechanism of action for Mannose 6-Phosphate has been proposed which is based on downregulation of M6P/IGF-II receptor and TGF-$\beta$1 mRNAs.

7 Claims, 3 Drawing Sheets

OTHER PUBLICATIONS

Moren A., et al., "Identification and characterization of LTBP–2, a novel latent transforming growth factor–β–binding protein", J. Biol. Chem., 1994, 269:32469–32478.

Yin W., Isolation of a novel transforming growth factor–β binding protein gene (LTBP–3), J. Biol. Chem., 1995, 270:10147–10160.

Schultz–Cherry et al., "Thrombospondin causes activation of latent transforming growth factor–β secreted by endothelial cells by a novel mechanism", J Cell Biol., 1993, 122:923–932.

Schultz–Cherry, S., "Regulation of transforming factor–β activation by discrete sequences of thrombospondin 1", J. Biol. Chem., 1995, 270:7304–7310.

Glick, A.B., Retinoic acid induces transforming growth factor β–2 in cultured keratinocytes and mouse epidermis, Cell Regulation 1989, 1:87–97.

Kojima S., "Mechanism of retinoid–induced activation of latent transforming growth factor–β in bovine endothelial cells", J. Cell Biol., 1993, 155:323–332.

Oreffo R.O.C., "Activation of the bone–derived latent TGF beta complex by isolated osteoclasts", Biochem. Biophys. Res. Commun., 158:817–823.

Colletta A.A., "Anti–estrogens induce the secretion of active transforming growth factor beta from human fetal fibroblasts", Br. J. Cancer, 1990, 62:405–409.

Flaumenhaft R., et al., "Role of latent TFG–β by co–cultures of endothelial and smooth muscle cells", J. Cell Biol., 1992, 118:901–909.

Boyan B., et al., "Latent transforming growth factor–β is produced by chrondrocytes and activated by extracellular matrix vesicles upon exposure to 1,25–(OH)$_2$D$_3$", J. Biol. Chem, 1994, 269:28374–28381.

Mitchen J., et al. "Use of microfluorimetric assay to measure proliferaative response of mink lung cells to purified TGF–β and to TGFβ activity found in prostate cell conditioned medium", In vitro Cell Dev. Biol.–Animal, 1995, 31:692–697.

Bizik J., et al., "Active transforming growth factor–β in human melanoma cell lines: no evidence for plasmin–related activation of latent TFG–β", J. Cell Biochem. 62:113–122(1996).

Huber D. et al., "Activation of human platelet–derived latent transforming growth factor–β1 by human glioblastoma cells", Biochem. J., 1991, 277:165–173.

Takeda K., et al., "Similar, but not identical, modulation of expression of extracellular matrix components during in vitro and in vivo aging skin fibroblasts", J. Cell. Physiol., 1992, 153:450–459.

Gosiewska A., et al., "Gene expression of iron–related proteins during iron deficiency caused by scurvy in guinea pigs", Arch. Biochem. Biophys., 1996, 325:295–303.

Knabee C. et al., "Evidence that transforming growth factor–β is a hormonally regulated negative growth factor in human breast cancer cells", Cell, 1987, 48:417–428.

Jones J.I., et al. "Insulin–like growth factors and their binding proteins: biological actions", Endocrinology, 1995, 16:3–34.

Humbel R.E., "Insulin–like growth factors I and II", Eur. J. Biochem, 1990, 190:445–462.

Gosiewska A. et al., "Evidence for an in vivo role of insulin–like growth factor–binding protein–1 and –2 as inhibitors of collagen gene expression in vitamin C–deficient guinea pigs", 1994, Endocrinology, 134:1329–1339.

Frantz F.W. et al., "Biology of fetal repair: The presence of bacteria in fetal wounds induces an adult–like healing response", J. Pediatric Surg., 1993, 28, 428–434.

Christensen M.K., et al., "Synthesis of mannose 6–phosphate–containing disaccharide threonine building blocks and their use in solid–phase glycopeptifde synthesis", J. Chem. Soc. Perkin Trans, 1993, 1:1453–1460.

Sato Y. et al., "Inhibition of endothelial cell movement by pericytes and smooth muscle cells: Activation of latent transforming growth factor–β–like molecule by plasmin during co–culture", J. Cell Biol. 1989, 109:309–315.

Kojima S., et al., "Lkpopolysaccharide inhibits activation of latent transforming growth factor–β in bovine endothelial cells", J. Cell. Physiol., 1995,163:210–219.

* cited by examiner

The treatments were as indicated:
1-PBS, 2-LPS,
3-LPS+M6P
and 4-LPS+DCA

FIG. 3

Untreated        Hydrocortisone

ANTI-FIBROTIC AGENT ASSAY

This application claims priority from U.S.S.N. 60/029,632 filed Oct. 25, 1996, now abandoned.

BACKGROUND OF THE INVENTION

Transforming Growth Factor β (TGF-β) is a potent growth regulatory protein and a key molecule implicated in various fibrotic (scarring) disorders. Most of the cells secrete TGF-β1 in a predominantly inactive high molecular weight form, latent TGF-β (L-TGF-β). Latent TGF-β is composed of an amino-terminal latency-associated peptide (LAP) non-covalently associated with the carboxyl-terminal mature TGF-β. The latency-associated peptide, is disulfide-bonded to a second, structurally unrelated protein, latent TGF-β binding protein (LTBP), which plays a role in the processing and secretion of TGF-β1 (1).

A major mechanism of regulating TGF-β activity occurs through factors which control the processing of the latent to biologically active form of the molecule. Physiochemical activation can occur by extremes of pH, heat, chaotropic agents (sodium dodecyl sulfate, urea) and deglycosylation (2, 3, 4, 5). Activation in vivo is more complex and not well understood.

Cell-mediated activation was first achieved by co-cultures of either pericytes or smooth muscle cells with capillary endothelial cells (6, 7). This method requires interaction of two cell types from the same species. The activation is apparently mediated by plasmin since activation is blocked by plasmin/serine protease inhibitors (8). Cellular activation is thought to require binding of the latent TGF-β to the mannose-6-phosphate/insulin-like growth factor II receptor (9) via the mannose-6-phosphate molecules found on the LAP component of the latent form of TGF-β (10). Tissue type II transglutaminase has also been demonstrated as a requirement for activation in this cell-dependent model which may function to crosslink latent TGF-β to the matrix molecules (11). The final requirement for activation involves the LTBP. It has been proposed that LTBP is necessary for concentrating the latent TGF-β complex onto the cell surface where it is subsequently activated, presumably by tissue transglutaminase and/or plasmin (12). Three different LTBP's have been identified and cloned (13–15) which may indicate a potential mechanism by which cells may control interactions of the latent TGF-β complexes with specific tissue sites or cell types. In addition, there are reports of TGF-β activation occurring independently of these mechanisms by binding of the latent complex to thrombospondin, an extracellular matrix associated glycoprotein (16, 17). Although L-TGF-β is not activated under normal culture conditions unless co-cultures are prepared, cells in homotypic cultures can be induced to form active TGF-β by application of specific agents. Among these agents are retinoids, which induce the activation of latent-TGF-β1 in keratinocytes, endothelial cells and osteoclasts (18, 19, 20). Retinoid-induced activation of TGF-β1 is dependent upon plasmin (18, 19). Anti-estrogens (tamoxifen or toremifine) induced the production of active TGF-β in fetal fibroblasts and mammary carcinoma cells (21). Exposure of bovine arterial or capillary endothelial cells to bFGF (basic Fibroblast Growth Factor) in vitro also resulted in activation of TGF-β apparently by a plasmin-dependent mechanism (22). Growth zone costochondral chondrocyte matrix vesicles were able to activate latent TGF-β when incubated with 1,25-dihydroxy vitamin D3 through a direct action of the vitamin on the extracellular matrix vesicle membrane (23).

In addition there are reports that small quantities of active TGF-β1 could be detected in conditioned media from human prostate epithelial cells (24), melanoma cell lines (25) and glioblastoma cells (26); however the mechanism of this activation is not understood.

To date, none of the systems generating active TGF-β1 has been utilized as a screening model for agents with the potential ability to sustain the latency of TGF-β1. The co-culture method has been studied extensively and the mechanisms responsible for activation of TGF-β1 in this system were elucidated. However, this co-culture method lacks reproducibility and has a strong requirement for screening large numbers of cell clones to produce an effective system.

The aim of these studies was to develop a new in vitro model for TGF-β activation for subsequent screening of molecules with potential abilities to interfere with its activation. Since TGF-β has been shown to be a key factor in scarring and fibrotic disorders, agents shown to be active in such an assay would be expected to function as anti-fibrotics and anti-scarring in vivo.

SUMMARY OF THE INVENTION

A novel method has been developed for screening and identifying modulators of scar formation, such as anti-scarring and anti-fibrotic agents. This method offers simplicity, it is reproducible and could be adopted to screen large number of modulator compounds to identify new potential anti-fibrotic agents.

This method has characteristics in common with the bovine arterial endothelial cells/bovine arterial smooth muscle cells (BAEC/BASMC) co-culture system, but is more sensitive and does not require screening large number of clonal lines for developing an effective method.

In this novel system, similar to the co-culture system, activation of L-TGF-β1 occurs by several independent mechanisms which involve binding of the latent complex to mannose-6 phosphate/insulin-like growth factor-II (M6P/IGF-II) receptors, thrombospondin and/or tissue type II transglutaminase. But, in contrast to the co-culture system, this macrophage-dependent system does not appear to involve plasmin.

Using this method, potential novel anti-fibrotic agents were identified, such as insulin-like growth factor II defined as IGF-II, (used separately or in combination with insulin-like growth factor binding protein-2 (IGFBP-2) as a delivery vehicle), tissue type II transglutaminase inhibitors and anti-inflammatory agents (such as hydrocortisone).

A novel mechanism of action for M6P has been proposed herein which is based on downregulation of M6P/IGF-II receptor and TGF-β1 mRNAs.

DETAILED DESCRIPTION OF THE INVENTION

Materials

D-mannose 6-phosphate, alpha-D(+)mannose 1-phosphate (M1P), monodansylcadaverine (DCA; substrate competitor for tissue type II transglutaminase, TGase II), cystamine (active site-directed inhibitor of TGase II), putrescine-dihydrochloride, DMSO (dimethyl sulphoxide oxide), LPS (lipopolysaccharide) from Salmonella abortus aqui, all-trans retinoic acid (RA) and hydrocortisone were obtained from Sigma Chemicals. Bovine serum albumin (BSA)-endotoxin free was purchased from Calbiochem. Stock solutions of retinoic acid and hydrocortisone were prepared in ethanol. Stock solutions were serially diluted into culture medium to yield a final concentration of 0.5%. This concentration of ethanol did not effect the production or activation of TGF-β1. Monodansylcadaverine stock solution was prepared in DMSO. The final concentration of DMSO (1:1000) used in the experimental conditions did not have effects on TGF β production or activation (data not shown). Recombinant human IGF-II was purchased from Bachem, Inc. Monoclonal neutralizing antibody against human urokinase plasminogen activator (uPA) was obtained from American Diagnostica, Inc. Monoclonal anti-human thrombospondin neutralizing antibody (clone I,A4.1) was purchased from Life Technologies. Recombinant human latent TGF-β1 (rHLTGF-β1) was obtained from R&D Systems. Sea Kem GTG agarose was from FMC, Bio Products. RNA size markers, Q X 174 DNA/Hae III markers and TGF-β1 ELISA kit were purchased from Promega. SuperScript™ II Rnase H⁻ Reverse Transcriptase was obtained from Life Technologies. AmpliTaq DNA Polymerase was obtained from Perkin Elmer Cetus. The RNeasy RNA extraction kit was purchased from Qiagen. All cell culture media were purchased from Life Technologies. Fetal Bovine Serum (FBS) was obtained from HyClone. Mouse peritoneal macrophages IC-21 transformed with SV-40, human fetal dermal fibroblasts (1502), human neonatal fibroblasts (43 SK) and human prostate adenocarcinoma cell line were obtained from American Type Culture Collection. The human melanoma cell lines Bowes and HMB-2 were received from Josef Bizik (Bratislava). Bovine arterial endothelial cells (BAEC) and bovine arterial smooth muscle cells (BASMC) were obtained from the Cell Application. Purified rat IGFBPs-1 and 2 (Insulin-like Growth Factor Binding Protein) were obtained from Dr. Beverly Peterkofsky (NIH, Bethesda, Md.).

Experimental Methods

Cell Culture

Mouse peritoneal macrophages IC-21 transformed with SV-40 were maintained in RPMI-1640 supplemented with 10% fetal bovine serum. Cultures were seeded in 100 mm dishes and grown in 5% $CO_2$ at 37° C. The medium was changed at 2-day intervals. Human fetal and neonatal dermal fibroblasts were grown in DMEM supplemented with 10% fetal bovine serum in the presence of 6 mM Hepes, 50 I.U./ml of penicillin and 50 mcg/ml of streptomycin. Cultures were seeded in 100 mm dishes and grown in 5% $CO_2$ at 37° C. The human melanoma cell lines Bowes and HMB-2 were maintained in Eagle's minimal essential medium (MEM) supplemented with 2 mM glutamine, 1% nonessential amino acids, 5% FBS and antibiotics. The cells were seeded in 100 mm dishes and grown in 5% $CO_2$ at 37° C. Human prostate adenocarcinoma cell line was grown in F 12K Nutrient Mix supplemented with 7% FBS, seeded in 100 mm dishes and grown in 5% $CO_2$ at 37° C. Bovine arterial endothelial cells were maintained in DMEM supplemented with 10% CS, glutamine and antibiotics. Smooth muscle cells were cultured in alpha MEM supplemented with 10% calf serum, glutamine and antibiotics. They were seeded in 100 mm dishes and grown in 5% $CO_2$ at 37° C.

Preparation of Conditioned Media (CM) from BAECs and BASMCs

The procedures for preparation of conditioned media were described previously (22). Briefly, for the retinoid experiment, BAEC cells were grown to confluency in 35 mm dishes. The cultures were rinsed with PBS (Phosphate Buffered Saline), and incubated in 1 ml of serum-free DMEM containing 0.1% of BSA and retinoic acid (10 μM) or vehicle (0.5% ethanol). The incubation was carried out for 24 h. The medium was aspirated, the cells were washed with PBS and then incubated in 1 ml of DMEM/0.1% BSA for an additional 12 h to produce conditioned medium. Conditioned media were centrifuged and used in the ELISA assay for TGF-β1 evaluation.

For co-culture experiments, BAECs and BASMCs were seeded separately in 35 mm dishes at a density of $40 \times 10^4$ cells in DMEM/10% CS (Calf Serum) or $3.2 \times 10^5$ BAECs and $0.8 \times 10^5$ BASMCs in the same 35-mm dishes. After cell attachment (approximately 2 h) the cells were rinsed with PBS and incubated in 1 ml of DMEM/0.1% BSA for 6 h to produce conditioned media. Conditioned Media were centrifuged and used in the ELISA assay.

Preparation of Conditioned Media from Cancer Cells

Melanoma cells (Bowes and HMB-2) and prostate adenocarcinoma cells were grown in 100 mm dishes to confluency. The media were aspirated, the cultures were washed with PBS and appropriate serum-free medium containing 0.1% BSA was applied for 24 h. The media were collected and stored for subsequent TGF-β1 evaluation by ELISA.

Macrophage Activation Assay

Activation of Macrophages with Lipopolysaccharides (LPS)

Figure 1:
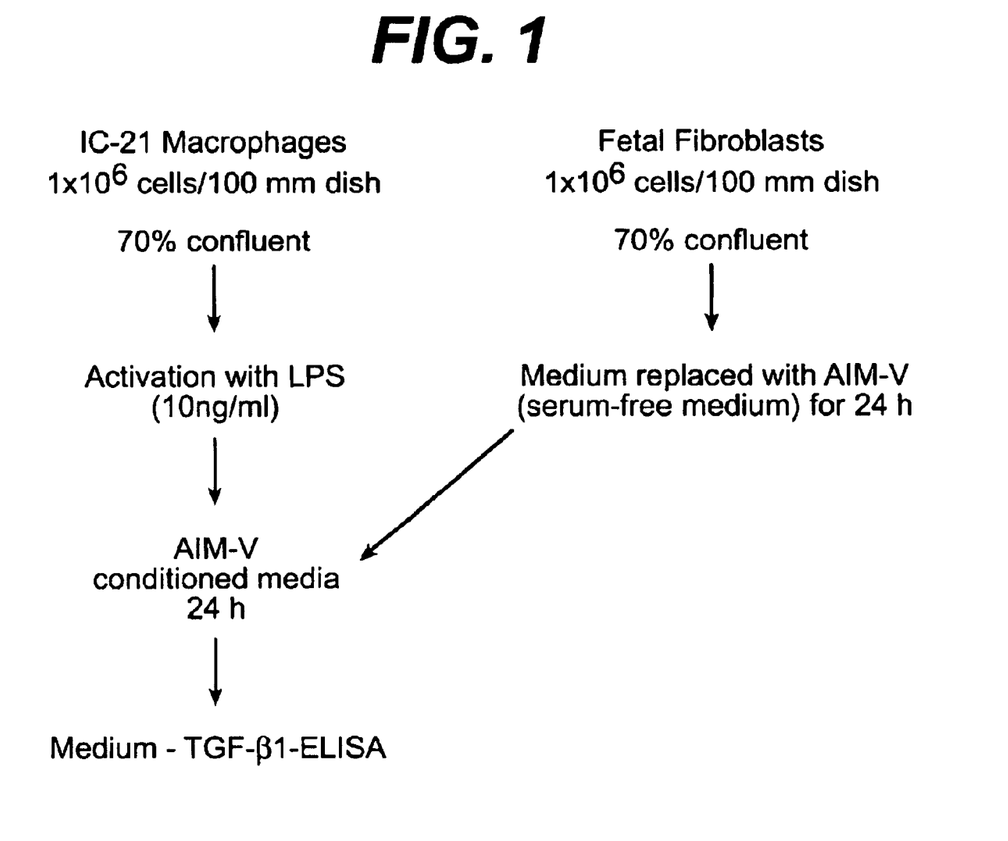
FIG. 1. Activation of TGF-β1 by macrophages is shown.

Cultured macrophages were lifted from the dish with 3 ml of PBS. The PBS was balanced with 15 ml of RPMI-1640 containing 10% FBS. The cells were counted and then seeded in 100 mm plates at $1 \times 10^6$ cells/dish. When the cultured macrophages reached approximately 70% confluency (2–3 days) they were washed with PBS and RPMI-1640 medium containing 5% FBS and 10 ng/ml LPS was applied (FIG. 1). After 24 h of activation with LPS the cells were washed gently with PBS. At this point conditioned medium from confluent fetal dermal fibroblasts was collected and 5 ml was distributed into each dish containing macrophages. The cells were incubated for an additional 24 h, the media were collected, spun down at 600×g for 10 min and stored at 4° C. before TGF-β1 evaluation by ELISA. Each condition was done in duplicate. The cells, washed with PBS, were harvested for total RNA extraction.

Preparation of Conditioned Media from Fetal Dermal Fibroblasts for the Macrophage Activation Assay Fetal dermal fibroblasts were seeded in 100 mm dishes at $1 \times 10^6$ cell/dish. The cells were grown to confluency (2–3 days). The cultures were washed with PBS and fresh medium, either DMEM supplemented with 10% FBS or AIM-V medium (a serum free medium) for serum-free conditions, was applied for 24 h (FIG. 1). The medium was collected and combined in order to obtain a homogenous pool of latent TGF-β1. The collection of the medium was done just prior to application in the macrophage assay.

Co-culture of Macrophages and Fetal Fibroblasts

For the experiments where macrophages and fetal fibroblasts were co-cultured, the two cell types were seeded in 100 mm dishes at a density of $1 \times 10^6$ fetal fibroblasts and $0.8 \times 10^6$ macrophages. After cell attachment (approximately 2 h) the cells were rinsed with PBS and incubated in 10 ml of RPMI-1640/5% FBS, +/− LPS for 24 h to produce conditioned media. Conditioned media were centrifuged as described above and used in the ELISA assay.

Treatment of Human Neonatal Fibroblasts with Mannose 6-Phosphate (M6P)

Human neonatal fibroblasts were seeded in 100 mm dishes at $1\times10^6$ cells/dish. When the cells reached confluency they were washed with PBS and the cultures were treated with different concentrations of M6P (1, 10, 50, 100, and 200 µM) for 24 and 48 h in serum-free conditions. In addition, cells were treated with two concentrations of Mannose 1-Phosphate (M1P) (100 and 200 µM) for 24 and 48 h. The total RNA was extracted and evaluated for the expression of M6P/IGF-II receptor, TGF-β1 and TGF-β receptor type I mRNAs by semi-quantitative reverse transcription polymerase chain reaction (RT-PCR). Each treatment was run in duplicates and repetitive analyses were performed.

ELISA for TGF-β1

ELISA tests were performed using a Promega kit and the protocol provided by the manufacturer was followed. Aliquots of the cell supernatants containing 10% FBS were diluted 1:4 or 1:20 for measurement of active and total TGF-β 1, respectively. Serum-free conditioned media were assayed undiluted for active and 10-times diluted for total TGF-β1. Each measurement was performed in duplicates. Color development was monitored with the use of a microplate reader (Molecular Devices) at 450 nm.

Total RNA Extraction

The cells were washed with PBS, followed by addition of the extraction buffer provided with the kit (RNeasy RNA extraction kit). The lysed cells were scraped from the dish and collected in microtubes. Samples were either frozen at −70° C. before analysis or directly assessed following manufacturer protocol. Absorbance at 260 nm and 280 nm was measured and the integrity of RNA was evaluated by denaturing formaldehyde agarose gels stained with ethidium bromide.

Northern Blot Analysis

Northern blot analysis was carried out as described previously (27). Briefly, total RNA samples (5 µg) were diluted in formaldehyde-MOPS buffer and subjected to electrophoresis in a denaturing 1.2% Sea Kem GTG agarose gel along with the RNA size markers. RNA was transferred to a nitrocellulose membrane by capillary transfer. The blots were prehybridized for 3 h at 42° C. in a solution containing 10% dextran sulfate, 2×Denhardt's solution, 50% formamide, 5×SSPE (0.75 M Sodium chloride, 0.05 M sodium phosphate, 0.005 M ethylenediaminetetraacetic acid)/0.1% SDS, and 250 µg/ml of sheared salmon testis DNA. Hybridization solution was essentially the same except that $^{32}P$ dCTP-labeled DNA probe and 150 µg/ml of salmon testis DNA were included. The hybridization was carried out for 16 h at 42° C. Post-hybridization washing steps were performed as follows: twice for 15 min with 2×SSC (0.75 M sodium chloride, 0.075 M sodium citrate) at 65° C., one for 30 min with 2×SSC/0.1% SDS at 65° C. and one for 10 min with 0.1×SSC at 65° C. Blots were exposed to X-Ray film with intensifying screens for 2 days at −80° C.

The probe used for hybridization was prepared by Reverse Transcriptase-Polymerase Chain Reaction (RT-PCR). Radiolabeling of cDNA probes was carried out by nick translation as described previously (27).

Reverse Transcriptase-Polymerase Chain Reaction

The procedure used to transcribe the total RNA was described in detail previously (28). Briefly, the reaction was carried out in a total volume of 25 µl containing 1× reverse transcriptase buffer (50 mM Tris-HCl, pH 8.3, 75 mM KCl, 3 mM MgCl$_2$), 10 mM DTT (Dithiothreitol), 2.5 mM each of dNTPs (Deoxynucleotides), 100 µg/ml of acetylated BSA, 4 units of rRNasin (ribonuclease inhibitor), 200 units of SuperScript™ RNase H⁻Reverse Transcriptase, 0.1 µg of oligo (dT)$_{12-18}$ and 1 µg of total RNA. Incubation was carried out for 1 h at 42° C. and was terminated by the addition of an equal volume of cold water.

A portion of the first strand cDNA reaction was used in PCR, which was carried out in 25 µl containing 16 mM Tris-HCl, pH 8.3, 50 mM KCl, 1.5 mM MgCl$_2$, 0.01% gelatin, 200 µM of each dNTPs, 1 µM each sense and antisense oligonucleotides and 2.5 units of AmpliTaq DNA polymerase. Amplification was carried out for 35 cycles. Each cycle consisted of: denaturation 1 min at 95° C.; annealing at 55° C. (optimal for the pair of oligonucleotides used) for 2 min; and elongation at 72° C., 3 min. For the final cycle elongation was 7 min. Reaction products were separated by 2% agarose gel electrophoresis and were visualized by ethidium bromide staining. Sizes were determined using Q X 174 DNA/Hae III markers. Restriction digests were performed in order to confirm PCR product specificity. Densitometry was used for quantitative analysis of the ethidium bromide stained gels.

The following examples illustrate the present invention without, however, limiting the same thereto.

EXAMPLES

It will be demonstrated that the inventive model has potential as a rapid method for screening and identifying anti-fibrotic (anti-scarring) agents. This system will also be useful in elucidating the mechanisms involved in TGF-β1 activation, and may increase our understanding of the nature of the interactions between TGF-β1 and other molecules present in the wound environment such as thrombospondin, IGFs and TGase II.

Example 1

BAEC Treated with Retinoic Acid (RA)

It has been reported that BAEC treated with retinoic acid (RA) produce detectable quantities of active TGF-β1 (19). Preliminary experiments were carried out to implement this method as a screening system for anti-fibrotic molecules. However, it was observed that even untreated BAEC cells produced active TGF-β1 (Table 1). This could be explained by the heterogeneity of the cell population; it is possible that a small number of contaminating cells, i.e. smooth muscle cells, contributed to this effect. In the presence of RA or vehicle (ethanol), the cells generated similar quantities of active TGF-β1 (Table 1). Mannose 6-Phosphate has been shown to block activation of TGF-β1 by competing with TGF-β binding to M6P/IGF-II receptor (9). However, when tested at 100 µM concentration in this system M6P had no significant inhibitory effects, similar to M1P (Table 1). These results indicate that the method may not be sufficient to evaluate anti-fibrotic molecules.

Comparative Example 2

Co-culture of BAEC and BASMC System

Preliminary experiments were carried out with the aim to adopt the published co-culture system for screening anti-fibrotic agents. This system is known to be plasmin dependent and has been shown to generate 2–5% of active TGF-β (22). In our hands co-culture of bovine arterial endothelial cells and bovine arterial smooth muscle cells generated up to 8.2% of active TGF-β (Table 1) as measured by ELISA. One of the problems observed during co-culture was very low reproducibility of the assay. Moreover, after few passages, cells completely lost the ability to activate TGF-β1. This was not surprising since co-culture requires screening of several clones of endothelial and smooth muscle cells for developing an effective system. Mannose 6-Phosphate, when tested at 100 μM, did not significantly inhibit TGF-β1 activation in this assay. Therefore it was decided not to proceed with this system further.

TABLE 1

Activation of TGF-β1 by BAEC +/− BASMC +/− RA

| Cells | Active TGF-β1 (pg/ml) | Total TGF-β1 (pg/ml) | % Active |
|---|---|---|---|
| BAEC Alone | 274 | 3100 | 8.9 |
| BAEC + ETOH | 315 | 3324 | 9.5 |
| BAEC + RA (10 μM) | 276 | 2667 | 10.3 |
| BAEC + RA + M6P | 287 | 3544 | 8.1 |
| BAEC + RA + M1P | 280 | 3686 | 7.6 |
| Co-culture | 56 | 687 | 8.2 |
| Co-culture + M6P | 58 | 770 | 7.5 |

Table Abbreviations:
BAEC-bovine arterial endothelial cells
RA-retinoic acid
M6P-mannose-6-phosphate
M1P-mannose-1-phosphate Characterization of TGF-β1 Activation Pathway by Cancer Cells It has been shown that cancer cells, such as human breast cancer, some melanoma cell lines and prostate adenocarcinoma cell lines, constitutively release biologically active TGF-β1 into the culture medium (24, 25, 29). Since the homotypic cell culture system would be of advantage due to its simplicity, an attempt was made to implement cancer cells as a method for TGF-β1 activation. It was shown that melanoma cell line Bowes secreted substantially more active TGF-β1 than HMB-2 cells and the percentage of active, relative to total TGF-β1, was approximately 29.3% and 4.2%, respectively. Human prostate adenocarcinoma cells produced less active TGF-β1 then melanoma cell lines (Table 2).

TABLE 2

Activation of TGF-β1 by Cancer Cells

| Cells | Active TGF-β1 (pg/ml) | Total TGF-β1 (pg/ml) | % Active |
|---|---|---|---|
| Bowes Melanoma | 198 | 675 | 29.3 |
| HMB-2 Melanoma | 46 | 1007 | 4.6 |
| Human Prostate Adenocarcinoma Cells | 18 | 815 | 2.2 |

In contrast to co-culture, it was shown that M6P, DCA and anti-thrombospondin antibodies had no effect on TGF-β1 activation in either melanoma or in prostate cancer cells (Table 3). These results indicated that the activation of TGF-β1 occurred independently of M6P/IGF-II receptor, TGase II or thrombospondin.

In order to determine if the activation of TGF-β1 by cancer cells occurs intracellularly or via extracellular processing of L-TGF-β1, conditioned media from fetal fibroblasts (source of L-TGF-β1) were applied to melanoma cells. However there was no further activation of TGF-β1 which suggested that the intracellular rather then extracellular mechanism is involved in the processing of the latent molecule (Table 3).

TABLE 3

Characterization of TGF-β1 activation by melanoma and prostate adenocarcinoma cells

| MECHANISM | TREATMENT | % ACTIVE TGF-β1 (STD) |
|---|---|---|
| BOWES | | |
| M6P/IGF II Receptor | M6P 100 μM | 113.5 (3.5) |
| Transglutaminase Type II | DCA 100 μM | 145 (0.34) |
| Thrombospondin | Anti-Thrombospondin 1:1500 dil | 85.9 (27) |
| Extracellular activation | AIM-V/1502 | 94.1 (8.4) |
| HMB-2 | | |
| M6P/IGF II Receptor | M6P 100 μM | 108.4 (17.9) |
| Transglutaminase Type II | DCA 100 μM | 110.7 (7.5) |
| Thrombospondin | Anti-Thrombodospondin 1:1500 dil | 97.2 (18.0) |
| Extracellular activation | AIM-V/1502 | 90.9 (11.7) |
| Adenocarcinoma Cells | | |
| M6P/IGF II Receptor | M6P 100 μM | 91.8 (8.5) |
| Transglutaminase Type II | Cystamine (100 μM) | 91.1 (3.0) |
| Thrombospondin | Anti-Thrombospondin 1:1500 dil | 107.1 (8.6) |

Table Abbreviations:
M6P-mannose-6-phosphate
DCA-dansylcadaverine

TGF-β Activation by Macrophages

The observation from previous studies that LPS treated macrophages were expressing higher levels of mRNA for TGase II than untreated cells indicated that these cells may be capable of activation of TGF-β1 by a TGase II-dependent mechanism. In order to test this hypothesis, macrophages were treated with LPS in the presence of fetal fibroblast conditioned media as a source of latent TGF-β1. It was speculated that addition of latent exogenous TGF-β1 into this system may increase the sensitivity of the assay since the level of total TGF-β1 produced by macrophages is relatively low (644 pg/ml in the presence of 10% FBS) as compared to the level observed in fibroblast conditioned media (1786 pg/ml).

Macrophages (MQ) secreted TGF-β1 predominantly in the latent form (Table 4). When the cells were treated with LPS (MQ+LPS) the level of active TGF-β1 was below the detection limit of ELISA. Similarly the level of active TGF-β1 in conditioned media from fetal fibroblasts (FF−CM), both in the presence of serum (FF−CM) as well as in serum-free media (FF−CM SF) was almost undetectable (7.2 and 5.7 pg/ml, respectively). In contrast, applying fibroblast conditioned media to macrophages (MQ+FF−CM) resulted in a 10-fold induction in the level of active TGF-β1 (Table 4). Treatment of macrophages with LPS prior to incubation with fibroblasts conditioned media resulted in a further activation of TGF-β1 (MQ+LPS+FF−CM).

The activation also occurred in serum-free conditions (MQ+FF−CM SF). Interestingly pre-treatment with LPS did not enhance the rate of activation of TGF-β1 (Table 4). This may indicate that serum cofactors are important in LPS-mediated activation.

TABLE 4

TGF-β1 Activation by Macrophages

| Treatment | Active TGF-β1 (pg/ml) |
|---|---|
| MQ | Undetectable |
| MQ + LYS | Undetectable |
| FF – CM | 7.2 |
| MQ + FF – CM | 71.1 |
| MQ + LYS + FF – CM | 154 |
| FF – CM (SF) | 5.7 |
| MQ + FF – CM (SF) | 98.3 |
| MQ + LYS + FF – CM (SF) | 93.3 |

Table Abbreviations:
MQ-macrophages
LPS-lipopolysaccharide
FF-fetal fibroblast
FF-CM-fetal fibroblast conditioned media
SF-serum free The substitution in the media with purified recombinant latent form of TGF-β1 was tested in an attempt to determine the requirement for fibroblast conditioned media in the macrophage assay. Only 3.3% of rHLTGF-β1 was activated by macrophages when the treatment with LPS was omitted (Table 5). When macrophages were treated with LPS prior to exposure to latent TGF-β1 the activation was higher and reached 12.2% (Table 5). This indicates that the sensitivity of the inventive system could be manipulated by LPS and that the amounts of latent TGF-β1 used initially for the activation could be titrated for maximal effects.

TABLE 5

Activation of rHLTGF-β1 by Macrophages

| Treatment | Active TGF-β1 (pg/ml) | Total TGF-β1 (pg/ml) | % Active |
|---|---|---|---|
| No LPS, 200 pg/ml rHLTGF-β1 | 10.9 (7.2) | 324 (7.2) | 3.3 |
| LPS, 200 pg/ml rHLTGF-β-1 | 48.8 (3.5) | 399 (44.5) | 12.2 |

Table Abbreviations:
LPS-lipopolysaccaride
rHLTGF-β1 -recombinant human latent TGF-β1

Co-culture of macrophages and fetal fibroblasts also resulted in the activation of TGF-β1. The level of active TGF-β1 was 16.0 pg/ml in LPS untreated and 14.4 pg/ml in LPS-treated macrophages, respectively (Table 6). Since the level of active TGF-β1 was relatively low, this system was not pursued further.

TABLE 6

Activation of TGF-β1 by Co-Cultures of Macrophages & Fetal Fibroblasts

| Treatment | Active TGF-β1 (pg/ml) | Total TGF-β1 (pg/ml) | % Active |
|---|---|---|---|
| Untreated | 16.0 (1.4) | 2535 | 0.6 |
| LPS Treated | 14.4 (0.2) | 2459 | 0.6 |

Table Abbreviations:
LPS-lipopolysaccharide

The experiments described here characterize a novel in vitro model for TGF-β1 activation of the present invention. The model utilizes mouse transformed macrophages and their ability to activate latent TGF-β1 supplied either with fibroblast conditioned medium or as a recombinant latent form. The inventive model offers several advantages over existing systems. To date, the co-culture model was the most defined and characterized system. However this inventive model offers higher sensitivity and is more efficient in terms of generation of active TGF-β1 than the co-culture system. The concentration of active TGF-β1 reported for co-culture system is approximately 15–50 pg/ml (22). This represents only 2–5% of total TGF-β1 present in co-culture conditioned medium (22). The amount of active TGF-β1 generated by macrophages in the method of the present invention is up to 10 times higher and represents up to 12% of total TGF-β1.

The method of the present invention is simple and is based on homotypic cell culture. In contrast, in the co-culture model, two cell types must be present and a number of requirements have to be fulfilled. The cell types must be either in contact or in very close proximity in order to produce active TGF-β1 since the co-culturing of endothelial cells on a surface 1–2 mm above a monolayer of smooth muscle cells fails to produce active TGF-β1 (35). A strong species specificity appears to exist as bovine arterial endothelial cells do not activate latent TGF-β1 in the presence of either human or pig smooth muscle cells (36). The sensitivity of this method of the present invention could be manipulated since the source of latent TGF-β1 which is activated by macrophages is not limited to fibroblast conditioned media. Recombinant latent TGF-β1 was converted to active form as well. One major disadvantage of the co-culture system is lack of reproducibility. Large numbers of BAEC and SMC cell clones need to be screened in order to develop an effective method. This requires isolation of a number of cell clones and subsequent laborious testing since the cells, after several population doublings, need to be replaced. In contrast, transformed macrophages as used in the present invention are capable of continuous culture and are readily available for routine analysis.

Another limitation of the co-culture model is the fact that this system fails to produce active TGF-β1 in the presence of LPS in the tissue culture medium (37) derived from the water or calf serum. It was reported that LPS found in the tissue culture medium downregulated the mRNA levels for TGase II and TGF-β1 in bovine arterial endothelial cells (37). This creates a need for testing each batch of tissue culture medium and serum for the presence of LPS in order to generate active TGF-β1. In contrast, the present disclosure showed that LPS-induced macrophages expressed higher levels of TGase II than untreated cells. This may indicate that LPS induces the activation of TGF-β1 through upregulation of TGase II levels in macrophages whereas it suppresses the activation of TGF-β1 by downregulation of TGase II in endothelial cells. It is also apparent that the method of the present invention is more versatile than the co-culture system.

Example 3

The Mechanisms of Activation of TGF-β1 in Macrophage Assay

An attempt was made to determine if the mechanisms involved in the activation of TGF-β1 in the are similar to those described for co-cultures of BAEC and BASMC. Several alternative mechanisms were tested, which involved M6P/IGF-II receptor, TGase II, thrombospondin and plasmin-dependent mechanisms. The results showed that, similar to co-culture, M6P at 100 and 50 $\mu$M inhibited TGF-β1 activation to 32.9%±11.5 and 69.6%±1.77 of control levels, respectively (Table 7). As expected, M1P, which does not bind to the M6P/IGF-II receptor, did not interfere with this activation (Table 7).

Dansylcadaverine (DCA), when tested at 100 $\mu$M, was a strong inhibitor since the level of active TGF-β decreased to 18.3%±1.55 of control levels (Table 6). In contrast, cystamine which was tested in the combination with M6P did not show additive effect on TGF-β1 activation (Table 6).

Putrescine, at two different concentrations tested (50 and 100 μM), also had some inhibitory effect since active TGF-β1 decreased to 33.4%±28.8 and 80.6±15.5 of control levels, respectively. Interestingly, the combination of both, M6P and putrescine (50 μM and 100 μM, respectively) did not have additive inhibitory effect on TGF-β1 activation (Table 7).

In contrast to the co-culture system, an antibody against urokinase plasminogen activator (uPA) tested at 400 ng/ml did not show any effect in the method of the present invention assay (Table 7). This indicates that plasmin is not involved in the activation of TGF-β1 in this inventive model. On the other hand, an antibody against thrombospondin inhibited TGF-β1 activation to 64.1%±6.0 of control (Table 7) which suggested that thrombospondin plays a role in this activation.

TABLE 7

Inhibition of TGF-β1 Activation by M6P, TGase II Inhibitors & Others

| Treatment | % Control (STD) |
| --- | --- |
| 50 μM M6P | 69.6 (1.7) |
| 100 μM M6P | 32.9 (11.5) |
| 100 μM M1P | 85.9 (28.2) |
| Dansylcadaverine 100 μM | 18.3 (1.6) |
| Putrescine 50 μM | 33.4 (28.8) |
| Putrescine 100 μM | 80.6 (15.5) |
| 50 μM M6P + 100 μM Putrescine | 57.4 (6.8 |
| 50 μM M6P + 100 μM Cystamine | 65.8 (11.3) |
| Anti-PA 400 ng/ml | 105.0 (4.8) |
| Anti-TSP 1:1500 dil | 64.1 (6.0) |

Table Abbreviations:
M6P-mannose-6-phosphate
M1P-mannose-1-phosphate
Anti-PA-antibody against plasminogen activator
Anti-TSP-antibody against thrombospondin The mechanisms involved in activation of TGF-β1 in the model method of the present invention are similar to those described for co-culture or homotypic cell culture system employing either BAEC or keratinocytes treated with RA. One aspect of the mechanism is the interaction of the latent TGF-β complex with the M6P/IGF-II receptor since the presence of M6P in the macrophage assay, similar to co-culture system, blocked the conversion of latent TGF-β1 to its active form. The second mechanism described in the co-culture system involved tissue Tgase II. The results of the assay method of the present invention showed that the presence of inhibitors of this enzyme prevented the generation of active TGF-β1 which indicates that TGase II plays a role in this activation. The molecular interaction of thrombospondin with latent TGF-β1 is sufficient to elicit biological activity in the co-culture system. Similarly, in the method of the present invention, antibodies against thrombospondin resulted in significant suppression of active TGF-β1 indicating that thrombospondin can contribute to the activation of the latent form. Plasmin has been shown to be required for the activation of TGF-β1 in the co-culture system. Antibodies against uPA efficiently blocked production of active TGF-β1 in co-cultures, but they were ineffective in the assay method of the present invention. This indicates that macrophages may activate TGF-β1 by a mechanism independent of plasmin activity.

The total TGF-β1 levels were evaluated after different treatments in the macrophage assay and it was apparent that total TGF-β1 was not significantly affected by the different treatments (Table 8).

TABLE 8

The concentration of total TGF-β1 after different treatments in the macrophage assay

| Treatment | Total TGF-β1 (STD) (pg/ml) |
| --- | --- |
| LPS + CM | 2418.7 (246) |
| M6P (100 μM) | 2472.6 (374.5) |
| DCA (100 μM) | 2302 (219.3) |
| LPS + CM (serum-free) | 1454.9 (76.7) |
| M6P 100 μM | 1649.8 (71.7) |

Figure 2:
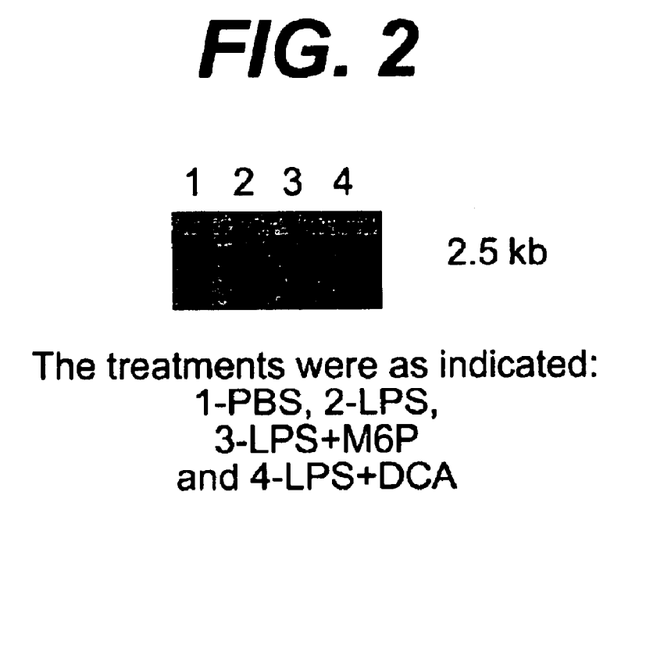
FIG. 2. The expression of mRNA for TGF-β1 in macrophages is shown.

Table Abbreviations:
LPS-lipopolysaccharide
CM-conditioned media
M6P-mannose-6-phosphate
DCA-dansylcadaverine Similarly, the levels of mRNA for TGF-β1 remained the same regardless of treatment of macrophages with PBS, LPS alone or combined treatments of LPS with M6P or DCA as measured by Northern blot (FIG. 2).

Example 4

Testing Potential Anti-fibrotic Agents in the Macrophage Assay

Using the assay method of the present invention several new potential anti-fibrotic molecules were identified. The effect of IGF-II on TGF-β1 activation was investigated since the occupancy of the M6P/IGF-II receptor with IGF-II could sterically inhibit binding of M6P on LAP to this receptor. It was shown that IGF-II inhibited TGF-β1 activation. The effect was specific since IGFBP-1 was able to reverse this inhibition by competing with the cell receptor for free ligand. On the other hand IGFBP-2 had no effect on IGF-II action in this system. This agrees with the results from previous in vivo and in vitro experiments that IGFBP-1 is a more potent inhibitor of IGF-mediated functions (32). Since IGFBP-2 did not interfere with IGF-II inhibitory effects on TGF-β1 activation, it may be used as a delivery vehicle for IGF-II in vivo by protecting against IGF-II degradation while permitting IGF-II action.

While IGF-II was not effective at 5 nM, higher concentrations (15 and 30 nM) had a dose-dependent inhibitory effect on TGF-β1 activation (Table 9). In addition, increasing concentrations of IGF-II (5 to 30 nM) were tested with constant concentration of M6P (50 μM). The results showed that the optimal inhibitory effect was achieved with 15 nM of IGF-II (Table 9) and the level of active TGF-β1 decreased to 38.7% of control (Table 9).

TABLE 9

Inhibition of TGF-β1 Activation by IGFs Family

| Treatment | % Control (STD) |
| --- | --- |
| IGF-II 5 nM | 105.6 (12.4) |
| IGF-II 15 nM | 65.1 (10.8) |
| IGF-II 30 nM | 54.3 (17.6) |
| IGF-II 5 nM + 50 μM M6P | 62.2 (15.5) |
| IGF-II 15 nM + 50 μM M6P | 38.7 (10.4) |
| IGF-II 30 nM + 50 μM M6P | 51.4 (17.6) |
| 50 μM M6P | 69.6 (1.7) |

Table Abbreviations:
IGF-II-insulin-like growth factor-II
M6P-mannose-6-phosphate Since IGF-II exists in the circulation or within the tissues as a complex form associated with IGFBPs (30, 31), two low molecular weight forms of IGFBPs, IGFBP-1 and 2 were tested for their ability to affect the inhibitory action of IGF-II. When tested separately or in combination with M6P, IGFBPs 1 and 2 did not show any significant inhibitory effects (Table 10). However, IGFBP-1, but not IGFBP-2, was able to reverse the IGF-II-mediated inhibitory effect on TGF-β1 activation. These results were confirmed when IGFBPs 1 and 2 were tested in the combination of IGF-II with M6P (Table 10). These results are in agreement with the previous findings that IGFBP-1 is a more potent inhibitor of IGFs-mediated functions than IGFBP-2 (32).

TABLE 10

Inhibition of TGF-β1 Activation by IGF-II and IGFBPs 1 and 2

| Treatment | % Control (STD) |
|---|---|
| IGF-II (15 nM) | 65.1 (10.8) |
| M6P (50 μM) | 69.6 (1.7) |
| IGFBP-1 (2 ng/ml) | 76.4 (8.7) |
| IGFBP-2 (2 ng/ml) | 77.9 (4.5) |
| IGFBP-1 + M6P | 77.4 (2.4) |
| IGFBP-2 + M6P | 70.9 (0.5) |
| IGFBP-1 + IGF-II | 97.6 (11.8) |
| IGFBP-2 + IGF-II | 55.5 (9.3) |
| IGFBP-1 + IGF-II + M6P | 76.5 (14.9) |
| IGFBP-2 + IGF-II + M6P | 35.5 (27.3) |

Table Abbreviations:
IGF-II-insulin-like growth factor-II
M6P-mannose-6-phosphate
IGFBP-1-insulin-like growth factor binding protein-1
IGFBP-2-insulin-like growth factor binding protein-2

Since fetal (scarless) wound healing is associated with no inflammatory reaction at the wound site as opposed to the inflammatory response observed in adult (scarring) wound healing (33) it was hypothesized that modulating the level of the inflammatory response could regulate the level of active TGF-β1 and presumably control the quality of the scar.

Anti-inflammatory agents were tested in the method of the present invention assay for their ability to modulate the levels of active TGF-1. It was apparent that hydrocortisone at 1 μM concentration inhibited TGF-β1 activation to 64.0% of control (Table 11).

TABLE 11

Inhibition of TGF-β1 by Hydrocortisone

| | Concentration | % Control (STD) |
|---|---|---|
| Hydrocortisone | 1 μM | 64.0 (0.4) |

Figure 3:
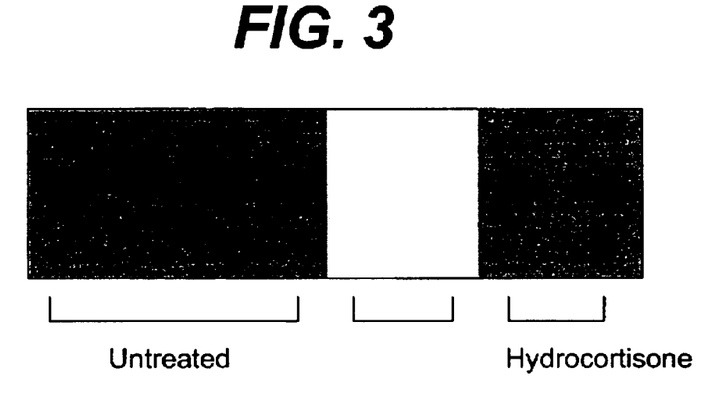
FIG. 3. The expression of mRNA for tissue Transglutaminase II in macrophages treated with hydrocortisone is shown.

In an attempt to identify the mechanism of this inhibition, the level of mRNA was evaluated for TGase II in macrophages treated with 1 μM hydrocortisone. Densitometric analysis of RT-PCR products (FIG. 3) revealed that the level of mRNA for TGase II was reduced to 37.5% by this treatment.

One of the important findings of this study is the potential anti-fibrotic action of hydrocortisone. Since treatment of macrophages with this agent downregulated TGase II mRNA levels, it is possible that hydrocortisone exerts its anti-fibrotic action through TGase II-dependent mechanism. In vivo use of anti-inflammatories may have the added value of not only reducing the level of inflammatory infiltrate but also reducing the accompanying high levels of growth factors including TGF-β and further affecting scar formation.

The assay method of the present invention demonstrated the reduction of active TGF-β1 for several classes of molecules including, TGase II inhibitors, M6P, IGF-II and the anti-inflammatory agent, hydrocortisone. The requirement for macrophages in this new assay allows for evaluation of anti-inflammatory agents which represent important potential anti-scarring therapies. The lack of such cells in the co-culture system would not permit its use to test anti-inflammatories.

M6P-anti-scarring Mechanism

In addition, a novel mechanism of action for M6P is reported herein. Downregulation of the level of mRNA occurs for M6P/IGF-II receptor and TGF-β1 in cultured fibroblasts after treatment with M6P. Furthermore, the decrease in the mRNA levels seems to be isoform specific since M1P did not show such effects.

Further experiments were designed with the aim to characterize the mode of action of M6P. Initial studies have shown that levels of the M6P/IGF-II receptors within the wounds treated with M6P were downregulated at 3 days post-wounding. This may provide another mechanism by which M6P may exert its function as an inhibitor of TGF-β1 activation. The expression of mRNA for M6P/IGF-II receptor was evaluated in human neonatal fibroblasts treated with several doses of M6P (1, 10, 50, 100 and 200 μM) for 24 and 48 h. The expression was not affected with 1–100 μM of M6P after 24 h of treatment. However treatment with 200 μM of M6P resulted in downregulation of the mRNA for the receptor (Table 13). After 48 h, the decrease was observed with 50–200 μM of M6P (Table 13). Similar downregulation was observed when the level of TGF-β1 mRNA was investigated after M6P treatment. On the other hand, the level of TGF-β receptor type I mRNA was unchanged during the time course of treatment. Mannose 1-Phosphate, tested at two highest concentrations (100 and 200 μM), showed no effects on both M6P/IGF-II receptor and TGF-β1 mRNA levels.

TABLE 13

The expression of M6P/IGF-II receptor and TGF-β1 cDNAs in neonatal fibroblasts measured by RT-PCR

| M6P (μM) | M6P/IGF-II Receptor 24 h | 48 h | TGF-β1 24 h | 48 h |
|---|---|---|---|---|
| 1 | 98.4 (20.6) | 112.8 (21.4) | 80.9 (11.1) | 86.3 (15.9) |
| 10 | 86.1 (3.2) | 108 (7.1) | 116.2 (25.1) | 78.8 (26.5) |
| 50 | 74 (36.6) | 59.3 (1.4) | 119.3 (24.4) | 75 (42.4) |
| 100 | 85.4 (25) | 42.2 (3.2) | 95.6 (31) | 57.5 (15.9) |
| 200 | 57.5 (5.2) | 39.6 (1.3) | 62.5 (27.7) | 28.8 (23) |

References

1. K. Miyazono, A Olofsson, P. Colosetti, C. H. Heldin. A role of the latent TGF-β-binding protein in the assembly and secretion of TGF-β1. *EMBO J.* 10: 1091–1101.
2. P. D. Brown, L. M. Wakefield, A. D. Levinson, M. B. Sporn. Physiochemical activation of recombinant latent transforming growth factor-betas 1, 2 and 3. *Growth Factors.* 1990, 3:35–43.
3. K. Miyazono, C. H. Heldin. Role for carbohydrate structures in TGF-β1 latency. *Nature* 1989, 338: 158–160.
4. K. Miyazano, U. Hellman, C. Wemstedt, C. H. Heldin. Latent high molecular weight complex of transforming growth factor β1; purification from human platelets and structural characterization. *J. Biol. Chem.* 1988, 263: 6407–6415.
5. R. Pircher, P. Jullien, D. A. Lowrence. β-transforming growth factor is stored in human blood platelets as a latent high molecular weight complex. *Biochem. Biophys. Res. Comm.* 1989, 163: 56–63.

6. A. Orlidge, P. A. D'Amore. Inhibition of capillary endothelial cell growth by pericytes and smooth muscle cells. *J. Cell Biol.* 1987, 105:1455–1462.
7. A. A. Antonelli-Orlidge, K. B. Saunders, S. R. Smith, P. D'Amore. An activated form of transforming growth factor beta is produced by co-cultures of endothelial cells and pericytes. *Proc. Natl. Acad. Sci. USA.* 1989, 86: 4544–4548.
8. Y. Sato, R. Tsuboi, R. Lyons, H. Moses, D. B. Rifkin. Characterization of the activation of latent TGF-β by co-cultures of endothelial cells and pericytes or smooth muscle cells. *J. Cell Biol.* 1990, 111:757–763.
9. P. A. Denis, D. B. Rifkin. Cellular activation of latent TGF-β requires binding to the cation-independent mannose-6-phosphate/insulin-like growth factor type II receptor. *Proc. Natl. Acad. Sci. USA.* 1991, 88:580–584.
10. A. F. Purchio, J. A. Cooper, A. M. Brunner, M. N. Lioubin, L. E. Gentry, K. S. Kovacina, R. A. Roth, H. Marquardt. Identification of mannose-6-phosphate in two asparagine-linked sugar chains of recombinant transforming growth factor-β1 precursor. *J. Biol. Chem.* 1988, 263:14211–14215.
11. S. Kojima, K. Nara, D. B. Rifkin. Requirement for transglutaminase in the activation of latent transforming growth factor-β in bovine endothelial cells. *J. Cell. Biol.* 1993, 121, 2:439–448.
12. R. Flaumenhaft, M. Abe, Y. Sato, K. Miyazono, J. Harpel, C. H. Heldin, D. B. Rifkin. Role of latent-TGF-β binding protein in the activation of latent TGF-β by co-cultures of endothelial and smooth muscle cells. *J. Cell Biol.* 1993, 4: 995–1002
13. T. Kanzaki, A. Olofsson, A. Moren, Ch. Wernsted, U. Hellman, K. Miyazano, L. Claesson-Welsh, C-H. Heldin. TGF-β1 binding protein: a component of the large latent complex of TGF-β with multiple repeat sequences. *Cell,* 1990, 61:1051–1061.
14. A. Moren, A. Anders, G. Stenman, P. Sahlin, T. Kanzaki, L. Claesson-Welsh, P. Ten Dijke, K. Miyazano, C-H. Heldin. Identification and characterization of LTBP-2, a novel latent transforming growth factor-B-binding protein. *J. Biol. Chem.* 1994, 269:32469–32478.
15. W. Yin, E. Smiley, J. Germiller, R. P. Mecham, J. B. Florer, R. J. Wenstrup, J. Bonadio. Isoloation of a novel transforming growth factor-β binding protein gene (LTBP-3). *J. Biol. Chem.* 1995, 270:10147–10160.
16. S. Schultz-Cherry, J. E. Murphy-Ullrich. Thrombospondin causes activation of latent transforming growth factor-β secreted by endothelial cells by a novel mechanism. *J Cell Biol.* 1993, 122: 923–932.
17. S. Schultz-Cherry, H. Chen, D. F. Mosher, T. M. Misenheimer, H. C. Krutzsch, D. D. Roberts, J. E. Murphy-Ullrich. Regulation of transforming factor-β activation by discrete sequences of thrombospondin 1. *J. Biol. Chem.* 1995, 270:7304–7310.
18. A. B. Glick. K. C. Flanders, D. Danielpour, S. H. Yuspa, M. B. Sporn. Retinoic acid induces transforming growth factor β-2 in cultured keratinocytes and mouse epidermis. *Cell Regulation* 1989, 1:87–97.
19. S. Kojima, D. B. Rifkin. Mechanism of retinoid-induced activation of latent transforming growth factor-β in bovine endothelial cells. *J. Cell Biol.* 1993, 155:323–332.
20. R. O. C. Oreffo, G. R. Mundy, S. M. Seyedin, L. F. Bonewald. Activation of the bone-derived latent TGF beta complex by isolated osteoclasts. *Biochem. Biophys. Res. Commun.* 158:817–823.
21. A. A. Colletta, L. M. Wakefield, V. Howell, K. E. P. van Roozendaal, D. Danielpour, S. R. Ebbs, M. B. Sporn, M. Baum. Anti-estrogens induce the secretion of active transforming growth factor beta from human fetal fibroblasts. *Br. J. Cancer,* 1990, 62:405–409.
22. R. Flaumenhaft, M. Abe, Y. Sato, K. Miyazano, J. Harpel, C-H. Heldin, D. B. Rifkin. Role of latent TGF-β binding protein in the activation of latent TGF-β by co-cultures of endothelial and smooth muscle cells. *J. Cell Biol.* 1992, 118:901–909.
23. B. Boyan, Z. Schwartz, S. Park-Snyder, D. D. Dean, F. Yang, D. Twardzik, L. F. Bonewald. Latent transforming growth factor-β is produced by chondrocytes and activated by extracellular matrix vesicles upon exposure to 1,25-$(OH)_2D_3$. *J. Biol. Chem.* 1994, 269:28374–28381.
24. J. Mitchen, D. Bletzinger, R Rago, G. Wilding. Use of microfluorimetric assay to measure proliferative response of mink lung cells to purified TGF-β and to TGFβ activity found in prostate cell conditioned medium. *In vitro Cell Dev. Biol.-Animal.* 1995, 31:692–697.
25. J. Bizik, D. Felnerova, M. Grofova, A. Vaheri. Active transforming growth factor-β in human melanoma cell lines: no evidence for plasmin-related activation of latent TGF-β. In press.
26. D. Huber, A. Fontana, S. Bodmer. Activation of human platelet-derived latent transforming growth factor-β1 by human glioblastoma cells. *Biochem. J.* 1991, 277:165–173.
27. K. Takeda, A. Gosiewska, B. Peterkofsky. Similar, but not identical, modulation of expression of extracellular matrix components during in vitro and in vivo aging of human skin fibroblasts. *J. Cell. Physiol.* 1992, 153:450–459
28. A. Gosiewska, F. Mahmoodian, B. Peterkofsky. Gene expression of iron-related proteins during iron deficiency caused by scurvy in guinea pigs. *Arch. Biochem. Biophys.* 1996, 325:295–303.
29. C. Knabee, M. E. Lippman, L. M. Wakefield, K. C. Flanders, A. Kasid, R. Derynck, R. B. Dickson. Evidence that transforming growth factor-β is a hormonally regulated negative growth factor in human breast cancer cells. *Cell,* 1987, 48:417–428.
30. J. I. Jones, D. R. Clemmons. Insulin-like growth factors and their binding proteins: biological actions. *Endocrinology.* 1995,16:3–34.
31. R. E. Humbel. Insulin-like growth factors I and II. *Eur. J. Biochem.* 1990, 190: 445–462.
32. A. Gosiewska, S. Wilson, D. Kwon, B. Peterkofsky. Evidence for an in vivo role of insulin-like growth factor-binding protein-1 and -2 as inhibitors of collagen gene expression in vitamin C-deficient guinea pigs. 1994, *Endocrinology,* 134:1329–1339.
33. F. W. Frantz, D. A. Bettinger, J. H. Haynes, D. E. Johnson, K. M. Harvey, H. P. Dalton, D. R. Yager, R. F. Diegelmann, I. K. Cohen. Biology of fetal repair: The presence of bacteria in fetal wounds induces an adult-like healing response. *J. Pediatric Surg.* 1993, 28, 428–434
34. M. K. Christensen, M. Meldal, K. Bock. Synthesis of mannose 6-phosphate-containing disaccharide threonine building blocks and their use in solid-phase glycopeptide synthesis. *J. Chem. Soc. Perkin Trans.* 1993, 1:1453–1460
35. R. Flaumenhaft, S. Kjima, M. Abe, D. R. Rifkin. Activation of transforming growth factor β. *Advances Pharm.* 1993, 24:51–76.
36. Y. Sato, D. B. Rifkin. Inhibition of endothelial cell movement by pericytes and smooth muscle cells: activation of latent transforming growth factor-β1-like molecule by plasmin during co-culture. *J Cell Biol.* 1989, 109:309–315

37. S. Kojima, R. Vemooy, D. Moscatelli, H. Amanuma, D. R. Rifkin. Lipopolysaccharide inhibits activation of latent transforming growth factor-β in bovine endothelial cells. *J. Cell. Physiol.* 1995, 163:210–219.

What is claimed is:

1. A method for identifying modulators of scar formation, comprising the steps of:
   (a) incubating immortalized, non-cancerous macrophages with an exogenous source of latent TGF-β1 and a modulator compound that modulates latent TBF-β1 activation;
   (b) measuring the amount of active TGF-β1 produced by the macrophages; and
   (c) comparing the measured amount of active TGF-β1 produced in step (b) with a control, the control being the measured amount of active TGF-β1 produced by the incubation of step (a) without the modulator compound of step (a) in order to identify the modulator compound's propensity for scar formation.

2. The method of claim 1, wherein the macrophages are LPS-stimulated.

3. The method of claim 1, wherein the macrophages are mouse peritoneal macrophages IC-21 transformed with SV-40.

4. The method of claim 2, wherein the macrophages are mouse peritoneal macrophages IC-21 transformed with SV-40.

5. The method according to any of the claim 2, 3, or 4, wherein the source of the exogenous, latent TGF-β1 is a conditioned cell culture medium from fetal fibroblasts.

6. The method of claim 5, wherein the cell culture medium contains serum.

7. The method according to any of the claim 1, 2, 3, or to 4, wherein the source of the exogenous, latent TGF-β1 is a recombinant latent form of TGF-β1.

* * * * *